United States Patent [19]

Hafeli

[11] Patent Number: 5,006,121

[45] Date of Patent: Apr. 9, 1991

[54] BONE BROACHES AND METHODS OF MANUFACTURING THEREOF

[75] Inventor: Paul B. Hafeli, El Toro, Calif.

[73] Assignee: Artifex Ltd., Newport Beach, Calif.

[21] Appl. No.: 513,070

[22] Filed: Apr. 23, 1990

[51] Int. Cl.⁵ .............................................. A61F 5/04
[52] U.S. Cl. ....................................... 606/85; 606/79
[58] Field of Search .................. 606/85, 80, 84, 79, 606/167–170; 623/22, 23

[56] References Cited

U.S. PATENT DOCUMENTS

| D. 273,806 | 8/1984 | Bolesky et al. | 606/85 |
|---|---|---|---|
| 4,552,136 | 11/1985 | Kenna | 606/85 |
| 4,601,289 | 7/1986 | Chiarizzio et al. | 606/85 |
| 4,671,275 | 6/1987 | Deyerle | 606/85 |
| 4,739,750 | 4/1988 | Masse et al. | 606/85 |

FOREIGN PATENT DOCUMENTS 2547192 12/1984 France ................................. 606/85

*Primary Examiner*—Max Hindenburg
*Assistant Examiner*—Gary Jackson
*Attorney, Agent, or Firm*—Blakely, Sokoloff Taylor & Zafman

[57] ABSTRACT

A bone broach and method of manufacture of the same for broaching the inside of a femur or other bone preparatory to the receipt of an implant, as in the installation of an artificial hip or the like. The borach is comprised of a support mandrel and a plurality of broach plates stacked on the mandrel and angularly referenced thereto, each of the broach plates having a peripheral surface shaped at least in part to form a cutting edge to define at least part of the desired bone opening for the respective axial position of that broach plate on the mandrel. In this manner, individual broach plates may be cut and finished as desired, so that once stacked on the mandrel in the appropriate order, the same collectively will define the desired three dimensional broach surface. Various embodiments are disclosed.

22 Claims, 1 Drawing Sheet

BONE BROACHES AND METHODS OF MANUFACTURING THEREOF

BACKGROUND OF THE INVENTION

1. Field of the Invention

The present invention relates to the field of prostheses, and more specifically to broaches for forming the inside surface of a bone for receipt of a complimentary prosthesis.

2. Prior Art

In recent years the replacement of joints, most frequently hips, in persons having damaged, diseased or malformed joints has become more and more frequent. Since hip replacement is the most common of such operations, the same will be described herein as exemplary of the present and the developing field in general.

In the case of hip replacements, some such operations involve the replacement of the ball or proximal end of the femur with a suitable prosthesis, while other such operations further include the installation of a socket or acetabular prosthesis also. In either event however, the top of the femur is prepared for receipt of the femoral component by drilling a cylindrical hole into the femur from the proximal end thereof, and then appropriately broaching or rasping out substantially all of the remaining cancellous bone so as to shape the same to be complimentary with both the neighboring cortical bone and the adjacent portion of the prosthesis to be installed therein. In many cases, a prosthesis of a standard size is to be installed, and accordingly standard size broaches may be used. Even in these cases however, it is common to provide and use more than one broach size, such as by way of example, a slightly undersized broach for rough forming of the bone opening, and a nominal size for finishing of the opening. Given the need for different size broaches for a given implant, and the various size implants available, standard broaches are now available in a broad range of sizes.

In the prior art, bone broaches were generally fabricated from a solid piece of metal. Since the prosthesis must in effect be supported by the inside of the bone, and the inner surface of the bone at the proximal end thereof is a complicated three dimensional contour, the cutting of a broach to accurately match this three dimensional contour requires special equipment for progressively generating the cutting edges which will define the desired three dimensional contour.

In some instances wherein special problems exist such as malformed hip joints, unusually large (or small) people, certain injuries and the like, special implants must be manufactured to match the specific patient involved, typically using scan or x-ray data for the patient taken before the manufacture of the custom prosthesis and of course well before the installation operation. Obviously, a non-standard prostheses in turn requires a selection of non-standard broaches for use in preparing the bone, which non-standard broaches if manufactured from a solid piece of material are even more expensive than standard broaches. It is therefore one purpose of the present invention to reduce the cost of such broaches by simplifying the manufacturing procedure to achieve in a much less costly manner, bone broaches for the desired contours and characteristic manufactured of appropriate materials. Another purpose of the invention is to achieve a better cutting action by allowing more flexibility in the broach cutting edge design, whether the broach is of a custom or standard design. Still another purpose is to provide a broach which may be more easily and accurately inspected to verify the cutting contours at various positions thereof, again whether of a custom or standard design.

BRIEF SUMMARY OF THE INVENTION

Bone broaches and methods of manufacture of the same for broaching the inside of a femur or other bone preparatory to the receipt of an implant, as in the installation of an artificial hip or the like. The broach is comprised of a support mandrel and a plurality of broach plates stacked on the mandrel and angularly referenced thereto, each of the broach plates having a peripheral surface shaped at least in part to form a cutting edge to define at least part of the desired bone opening for the respective axial position of that broach plate on the mandrel. In this manner, individual broach plates may be cut and finished as desired, so that once stacked on the mandrel in the appropriate order, the same collectively will define the desired three dimensional broach surface. Various embodiments are disclosed.

DETAILED DESCRIPTION OF THE INVENTION

Figure 1:
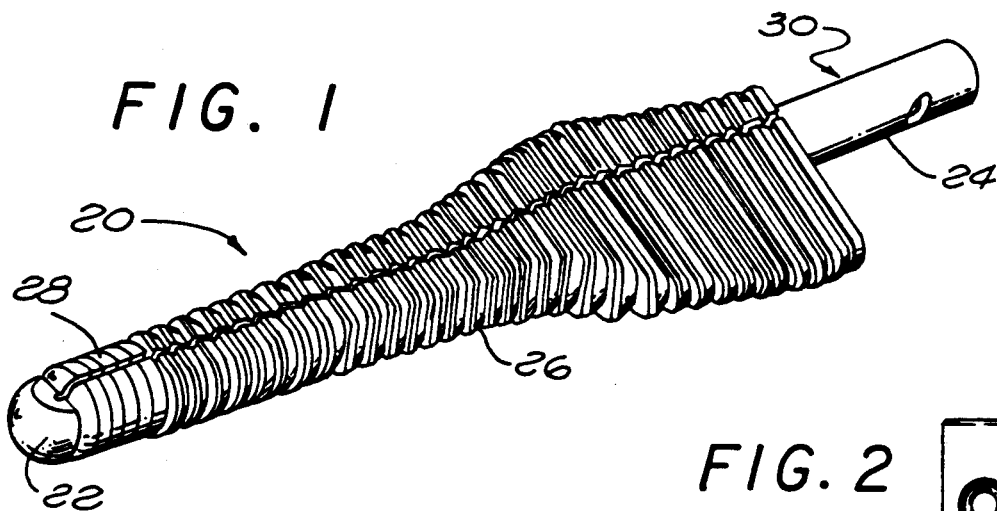
FIG. 1 is a perspective view of a broach of the present invention.

First referring to FIG. 1, a perspective view of a completed broach in accordance with the present invention may be seen. Like prior broaches, the same is characterized by a forward or distal end 22 of the broach and a shaft-like extension 24 at the aft or proximal end of the broach. The cutting portion of the broach 26 is characterized by a plurality of cutting edges, each oriented in a plane perpendicular to the axis of cylindrical section 28 and extension 24 (hereinafter the axis of the broach) with the various cutting edges being located at different axial positions spaced along the axis of the broach, and of course contoured to coincide with the desired bone opening of the corresponding axial position. The individual cutting edges, as shall be subsequently described in greater detail, are defined by individual broach plates stacked on the broach mandrel, generally indicated by the numeral 30, between the proximal portion 24 of the mandrel and section 28 of the broach, and are clamped in position by rotating end 22 integral with the broach mandrel to thread the opposite end thereof tightly into the shaft-like extension 24. Section 28 in the embodiment shown is cylindrical, though shapes other than cylindrical may readily be used as desired.

Figure 2:
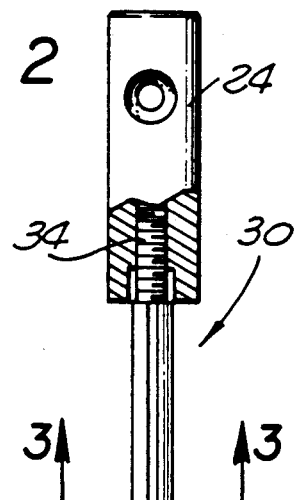
FIG. 2 is a side view of the mandrel 30 of the broach of FIG. 1.
Figure 3:
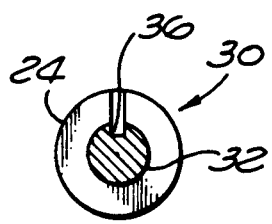
FIG. 3 is a cross section taken along line 3—3 of FIG. 2.

Now referring to FIGS. 2 and 3, a side view and a cross section of the broach mandrel assembly 30 of FIG. 1 may be seen. The mandrel assembly of this embodiment is a two piece mandrel comprising a proximal portion 24 into which mandrel 32 on which individual broach plates are to be stacked is threaded. The forward end 34 of the mandrel has an end member 28 integral therewith (FIG. 1), with region 32 having a slot or keyway 36 cut therein extending all the way from the proximal end of the mandrel 30 through the full length of region 32, terminating in the end member 28.

Figure 4:
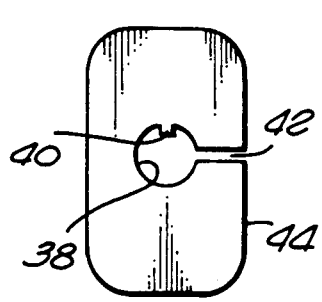
FIG. 4 is a platform view of a typical broach plate blank for a broach plate of the broach of FIG. 1.
Figure 5:
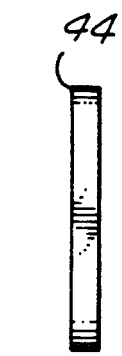
FIG. 5 is a side view of the broach plate blank of FIG. 4.
Figure 6:
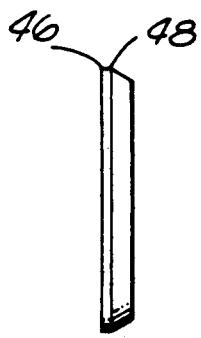
FIG. 6 is a side view of a finished broach plate.

The individual cutting edges in the central region 26 (FIG. 1) of the broach are defined by individual broach plates shown in FIGS. 4 through 6. In that regard, FIG. 4 shows a planform view of a broach plate of one embodiment of the invention, with FIG. 5 showing a broach plate blank prior to the finishing thereof and FIG. 6 showing the side view of a finished broach plate. The broach plate platform shown in FIG. 4 is characterized by an inner diameter 38 interrupted by an inward projecting tab 40 and a slot 42, with an outer peripheral surface 44 contoured and positioned with respect to the axis of the inner diameter 38 so as to reproduce in shape and location, the desired broach cutting surface for the axial position the particular broach plate is intended to occupy on the stack of broach plates on the mandrel. As may be seen in FIG. 5, the periphery 44 of the broach plates is straight and substantially perpendicular to the surfaces thereof.

The tab 40 interrupting the inner diameter 38 of each of the broach plates is proportioned to fit within the slot 36 in the mandrel 30 to angularly orient each of the broach plates to the mandrel and thus to each other, as in general the desired shape of the broach at each axial station will be something other than round, and frequently will not be centered on the axis of the mandrel. The slot 42 in the embodiment illustrated serves no particular function in the final broach, but rather is present because of the method of manufacture of the same. In particular, in the embodiment illustrated, the individual broach plates are cut from plate material using a wire EDM machine, the slot being cut thereby to avoid having to pre-drill a hole in the plate for each broach plate and to rethread the wire through each of such holes for each broach plate.

The broach plate blanks of FIG. 5 are each finished as illustrated in FIG. 6, by grinding the periphery 44 to the desired relief angle, leaving a short section as originally cut to provide the final cutting edge 46 thereon. The relief angle will provide a relief to reduce the resistance to the broach plate entering and cutting of the soft bone tissue, and will further provide space for the accumulation of the debris shaved away by the cutting action of the next succeeding broach plate in the broach plate stack.

Once the individual broach plates have been completed by the formation of the final cutting edge 46, the same are stacked in proper order on the mandrel 30 against the end 22, the assembly being clamped in position by rotating end 22 to thread the proximal end of mandrel 32 into shaft-like extension 24. For pilot purposes, the first few "broach plates" may be cylindrical or of other predetermined shape to pilot the same with respect to the hole drilled in the bone, with the forwardmost end of the broach being tapered somewhat to assist in this piloting function.

In the preferred embodiment for custom broaches, scans or x-rays are taken of the appropriate region of the patient's bone at regular intervals, such as every three millimeters or every 1.5 millimeters. Similarly, the broach plates themselves maybe cut from plate of a corresponding thickness. In general however, the scan or x-ray data will be angled with respect to the broach mandrel axis, and not directly applicable for broach plate manufacture. Instead, the scan data or x-ray is used for the prosthesis design, with the prosthesis shape then being sectioned for broach plate design.

Figure 7:
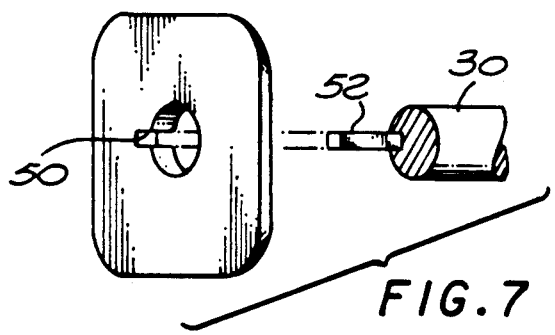
FIG. 7 is a perspective view of a typical broach plate and key of an alternate embodiment of the present invention.

Obviously of course, while the cutting of the broach plates through the use of an EDM machine as described herein is suitable, other fabrication techniques may also be used. By way of example, EDM machining may be used as described, but the angular position of the slot varied between adjacent broach plates so that any two broach plates together will provide a continuous cutting edge around the periphery of the broach. Similarly, broach plates have been cut using a $CO_2$ laser. Obviously however, more conventional machining techniques may also be used. By way of example, FIG. 7 illustrates an alternate form of broach plate wherein rather than the tab 40 being defined within diameter 38 of the broach plate, a slot 50 is cut therein so that the combination of the slot 50 and key 52 will provide the desired reference to the keyway or slot 36 in the mandrel 30. The slot 50 itself may be readily broached using conventional broaches, though of course either the same must be accurately angularly referenced to the broach plate periphery, or alternatively, the broach plate 50 should be subsequently defined and accurately referenced to the slot. Another method of manufacture of the broach plate is to first cut broach blanks, and then to mill the desired contour thereon with an angled cutter so as to define both the sharp cutting edge of appropriate planform and the relief using a numerically controlled vertical mill.

Figure 8:
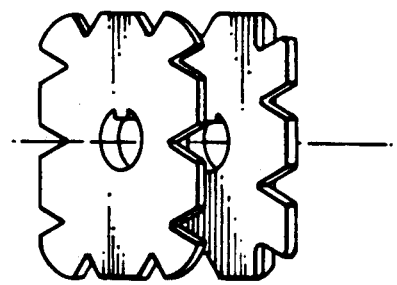
FIG. 8 is a perspective view of serrated broach plates wherein the cutting surface length of each broach plate is reduced and the desired bone opening at the corresponding axial position or positions is defined by two (or more) broach plates.
Figure 9:
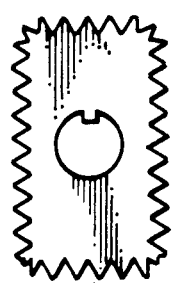
FIG. 9 is a perspective view of toothed broach plates in accordance with a still further alternate embodiment of the present invention.

The broaches of the embodiments hereinbefore described can be very accurately fabricated, and provide for the accurate broaching of the bone opening to the desired geometry, as the total length of cutting edge active at any one time defining such geometry is quite high. This in turn however, may tend to raise the force required to insert the broach. Accordingly, it may be desired in some instances to reduce the total length of active cutting edge. Thus by way of example, the broach plates may be toothed as illustrated in FIG. 8, with the tooth position being staggered between broach plates so that the cutting edge of two (or more) broach plates is combined to define the desired bone opening for the corresponding axial position or positions of the broach plates on the broach assembly. Obviously, the width of each cutting surface segment may be controlled as desired, ranging from the combined segments of any one broach plate defining substantially the entire periphery of the corresponding bone opening, to only a small percentage thereof as desired. Carried to the limit, each broach plate might have a toothed periphery as shown in FIG. 9, with the teeth being staggered between broach plates so that again two or more broach plates actually define the desired bone opening for the corresponding axial position or positions of the broach plates.

In the embodiment hereinbefore described in detail, the mandrel 32 (FIG. 2) was shown as a straight mandrel. In some cases it may not be possible to use a straight mandrel or at least a straight mandrel of the desired size because of the bone curvature over the distance to be cut by the broach. In such case, curved mandrels may be used, preferably being first manufactured straight and then bent with the desired curvature before the broach plates are stacked thereon. Also, if desired, broach plates may be cemented to each other, whether a curved or straight mandrel is used, to prevent any possible shifting of the broach plates with respect to each other. Finally, broaches may be fabricated in accordance with the present invention without using a mandrel at all, such as, by way of example, utilizing a central cable rather than a mandrel, or by cementing the broach plates to each other to form a rigid stack, though at least some means of retrieving the broach plates from within the bone in the event a bond fails may be desired, such as by way of example, a relatively small mandrel or alternatively a central flexible cable anchored in an end piece such as end piece 22 (see FIG. 1) and accessible from the proximal end of the broach. In any of these configurations, including those utilizing a mandrel, the broach plates could be angularly referenced to each other rather than each being angularly referenced to the mandrel, as in the embodiment herein before described in detail.

There has been disclosed and described herein a new and unique bone broach which may be readily fabricated in standard as well as non-standard sizes to high accuracy, and readily inspected to verify the same. While the invention has been disclosed and described with respect to certain preferred embodiments thereof, it will be understood by those skilled in the art that various changes in form and detail may be made therein without departing from the spirit and scope of the invention.

I claim:

1. A bone broach for removing tissue and shaping the surface of a bone for receiving an implant comprising:
    a support mandrel defining a mandrel axis and having first and second mandrel ends;
    a plurality of broach plates stacked on said mandrel between said first and second ends thereof, each broach plate having an opening therethrough through which said mandrel passes, and first and second substantially flat and parallel surfaces substantially perpendicular to said mandrel axis circumscribed by a peripheral surface shaped at least in part to form a cutting edge defining at least part of the desired bone opening for the respective axial position of the respective said broach plate on said mandrel;
    alignment means for maintaining each of said broach plates at a fixed angular alignment on and with respect to said mandrel; and,
    clamping means for maintaining said broach plates tightly stacked on said mandrel.

2. The bone broach of claim 1 wherein said alignment means comprises a longitudinal slot along said mandrel and means for angularly referencing each of said broach plates to said longitudinal slot.

3. The bone broach of claim 2 wherein said means for angularly referencing each of said broach plates to said longitudinal slot comprises a tab in said opening of each said broach plate for fitting within said slot.

4. The bone broach of claim 1 wherein each broach plate is circumscribed by a peripheral surface shaped to form a cutting edge defining the desired bone opening for the respective axial position of the respective said broach plate on said mandrel.

5. The bone broach of claim 1 wherein each said broach plate is circumscribed by a peripheral surface shaped to form a cutting edge defining only a portion of the desired bone opening for the respective axial position of the respective said broach plate on said mandrel, said cutting edges of neighboring broach plates defining other portions of the desired bone opening for the respective axial position of the respective said broach plate, whereby a plurality of neighboring broach plates together approximately define an entire desired bone opening.

6. The bone broach of claim 1 wherein said broach plates are stacked on said mandrel over said second end thereof, said mandrel having a stop flange thereon adjacent said first end thereof against which said broach plates are stacked, said second end of said mandrel being threaded, said clamping means being threaded onto said second end of said mandrel to clamp said stack of broach plates between said clamping means and said stop flange, said mandrel being insertable first end first into a bone to broach out the interior thereof.

7. A bone broach for removing tissue and shaping the surface of a bone for receiving an implant comprising:
    a support mandrel defining a mandrel axis and having first and second mandrel ends;
    a plurality of broach plates stacked on said mandrel between said first and second ends thereof, each broach plate having an opening therethrough through which said mandrel passes, and first and second substantially flat and parallel surfaces substantially perpendicular to said mandrel axis circumscribed by a peripheral surface shaped to form a cutting edge defining the desired bone opening for the respective axial position of the respective said broach plate on said mandrel;
    alignment means for maintaining each of said broach plates at a fixed angular alignment on and with respect to said mandrel;
    clamping means for maintaining said broach plates tightly stacked on said mandrel;
    said broach plates being stacked on said mandrel from said second end thereof, said mandrel having a stop flange thereon adjacent said first end thereof against which said broach plates are stacked, said second end of said mandrel being threaded, said clamping means being threaded onto said second end of said mandrel to clamp said stack of broach plates between said clamping means and said stop flange, said mandrel being insertable first end first into a bone to broach out the interior thereof.

8. A bone broach for removing tissue and shaping the surface of a bone for receiving an implant comprising:
    a support mandrel defining a mandrel axis and having first and second mandrel ends;
    a plurality of broach plates stacked on said mandrel between said first and second ends thereof, each broach plate having an opening therethrough through which said mandrel passes, and first and second substantially flat and parallel surfaces substantially perpendicular to said mandrel axis circumscribed by a peripheral surface shaped in part to form a cutting edge defining only part of the desired bone opening for the respective axial position of the respective said broach plate on said mandrel, said cutting edges of neighboring broach plates defining other portions of the desired bone opening for the respective axial position of the respective said broach plate, whereby a plurality of neighboring broach plates together approximately define an entire desired bone opening;

alignment means for maintaining each of said broach plates at a fixed angular alignment on and with respect to said mandrel; and, clamping means for maintaining said broach plates tightly stacked on said mandrel;

said broach plates being stacked on said mandrel from said second end thereof, said mandrel having a stop flange thereon adjacent said first end thereof against which said broach plates are stacked, said second end of said mandrel being threaded, said clamping means being threaded onto said second end of said mandrel to clamp said stack of broach plates between said clamping means and said stop flange, said mandrel being insertable first end first into a bone to broach out the interior thereof.

9. A method of fabricating a bone broach for removing tissue and shaping the surface of a bone for receiving an implant comprising the steps of:

providing a support mandrel defining a mandrel axis and having first and second mandrel ends;

forming a plurality of substantially flat broach plates, each having an opening therethrough for fitting over the mandrel and a means for angularly referencing the broach plate with respect to the mandrel, each broach plate being formed with a peripheral surface shaped at least in part to form a cutting edge defining at least part of a desired bone opening associated with the intended position of the respective broach plate in an ordered stack of the plurality of broach plates; and, fastening the broach plates on said mandrel, each in its intended position to form the ordered stack;

whereby the collective cutting edges form the desired broach shape.

10. The method of claim 9 further comprising of the step of determining the desired bone openings associated with the intended positions of the respective broach plates in an ordered stack of the plurality of broach plates by measuring the bone of the individual patient.

11. A method of fabricating a bone broach for removing tissue and shaping the surface of a bone for receiving an implant comprising the steps of:

providing a support mandrel defining a mandrel axis and having first and second mandrel ends;

forming a plurality of substantially flat broach plates, each having an opening therethrough for fitting over the mandrel and a means for angularly referencing the broach plate with respect to the mandrel, each broach plate being formed with a peripheral surface shaped to form a cutting edge defining a desired bone opening associated with the intended position of the respective broach plate in an ordered stack of the plurality of broach plates; and, fastening the broach plates on said mandrel, each in its intended position to form the ordered stack;

whereby the collective cutting edges form the desired broach shape.

12. The method of claim 11 further comprising of the step of determining the desired bone openings associated with the intended positions of the respective broach plates in an ordered stack of the plurality of broach plates by measuring the bone of the individual patient.

13. A method of fabricating a bone broach for removing tissue and shaping the surface of a bone for receiving an implant comprising the steps of:

providing a support mandrel defining a mandrel axis and having first and second mandrel ends;

forming a plurality of substantially flat broach plates, each having an opening therethrough for fitting over the mandrel and a means for angularly referencing the broach plate with respect to the mandrel, each broach plate being formed with a peripheral surface shaped to form a cutting edge defining only a portion of the desired bone opening for the intended position of the respective broach plate in an ordered stack of the plurality of broach plates on, the cutting edges of neighboring broach plates in the ordered stack of the plurality of broach plates being formed to define other portions of the desired bone opening for the respective axial position of the respective said broach plate, whereby a plurality of neighboring broach plates together approximately define an entire desired bone opening fastening the broach plates on said mandrel, each in its intended position to form the ordered stack;

whereby the collective cutting edges form the desired broach shape.

14. The method of claim 13 further comprising of the step of determining the desired bone openings associated with the intended positions of the respective broach plates in an ordered stack of the plurality of broach plates by measuring the bone of the individual patient.

15. In a bone broach for removing tissue and shaping the surface of a bone for receiving an implant, the improvement comprising:

a plurality of broach plates stacked between first and second ends of the bone broach, each broach plate having first and second substantially flat and parallel surfaces circumscribed by a peripheral surface shaped at least in part to form a cutting edge defining at least part of the desired bone opening for the respective axial position of the respective said broach plate in said stack, and means for maintaining said broach plates in an ordered, tightly stacked relationship.

16. The bone broach of claim 15 wherein said broach plates are cemented together.

17. The bone broach of claim 15 wherein said broach plates are stacked on another member.

18. The bone broach of claim 17 wherein said other member is a mandrel.

19. The bone broach of claim 17 wherein said other member is a straight mandrel.

20. The bone broach of claim 17 wherein said other member is a curved mandrel.

21. The bone broach of claim 17 wherein said other member is a flexible cable.

22. In a method of fabricating a bone broach for removing tissue and shaping the surface of a bone for receiving an implant, the improvement comprising the steps of:

(a) forming a plurality of broach plates stacked between first and second ends of the bone broach, each broach plate having first and second substantially flat and parallel surfaces circumscribed by a peripheral surface shaped at least in part to form a cutting edge defining at least part of the desired bone opening for the respective axial position of the respective broach plate in an ordered stack, and (b) stacking the broach plates in the ordered, tightly stacked relationship.

* * * * *

UNITED STATES PATENT AND TRADEMARK OFFICE
CERTIFICATE OF CORRECTION

PATENT NO. : 5,006,121
DATED : April 9, 1991
INVENTOR(S) : Hafeli

It is certified that error appears in the above-indentified patent and that said Letters Patent is hereby corrected as shown below:

In the Abstract at the 4th line "borach" should be --broach--.

Signed and Sealed this

Twenty-seventh Day of June, 1995

Attest:

BRUCE LEHMAN

Attesting Officer

Commissioner of Patents and Trademarks